United States Patent
Riedner et al.

(12)

(10) Patent No.: US 6,344,649 B2
(45) Date of Patent: *Feb. 5, 2002

(54) SCINTILLATOR FOR A MULTI-SLICE COMPUTED TOMOGRAPH SYSTEM

(75) Inventors: Robert J. Riedner, Waukesha; Erdogan O. Gurmen, Shorewood; David M. Hoffman, New Berlin, all of WI (US); August O. Englert, Cape Coral, FL (US); Timothy J. Sporer, Muskego; Matthew R. Schedler, Whitefish Bay, both of WI (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/977,439

(22) Filed: Nov. 26, 1997

(51) Int. Cl.[7] .................................................. G01T 1/20
(52) U.S. Cl. ........................................ 250/367; 250/368
(58) Field of Search ........................ 250/483.1, 486.1, 250/484.2, 367, 368

(56) References Cited

U.S. PATENT DOCUMENTS

| | | | | |
|---|---|---|---|---|
| 3,041,228 A | * | 6/1962 | MacLeod | 156/67 |
| 4,533,489 A | * | 8/1985 | Utts et al. | 250/301.7 |
| 4,615,583 A | * | 10/1986 | Tsuno et al. | 385/126 |
| 5,059,800 A | * | 10/1991 | Cueman et al. | 250/367 |
| 5,227,633 A | | 7/1993 | Ryuo et al. | |
| 5,329,124 A | * | 7/1994 | Yamamoto et al. | 250/367 |
| 5,378,894 A | * | 1/1995 | Akai | 250/368 |
| 5,831,269 A | * | 11/1998 | Nakamura et al. | 250/367 |
| 5,866,908 A | * | 2/1999 | Novak | 250/368 |

OTHER PUBLICATIONS

Applicants wish to call to Examiner's attention co-pending U.S. Application No. 08/977,441, filed Nov. 25, 1997 (sic) (PTO records may incorrectly indicate Nov. 25, 1997 but actual filing date is Nov. 26, 1997).

* cited by examiner

Primary Examiner—Constantine Hannaher
Assistant Examiner—Albert Gagliardi
(74) Attorney, Agent, or Firm—Carl B. Horton, Esq.; Armstrong Teasdale LLP

(57) ABSTRACT

Apparatus and methods for fabricating scintillators for use in a CT systems are described. Adjacent scintillator elements are separated by gaps filled with a composition of white diffuse reflective material, a light absorber, and a castable polymer. The composition increases the strength of the signal to the photodiode by minimizing the amount of light that is lost by the scintillator elements. Additionally, the light absorber minimizes the amount of light transferred between adjacent scintillator elements to limit cross-talk. In addition, the outer edges of the scintillator may have a lower amount of light absorber to compensate for the light lost from the periphery.

7 Claims, 3 Drawing Sheets

SCINTILLATOR FOR A MULTI-SLICE COMPUTED TOMOGRAPH SYSTEM

FIELD OF THE INVENTION

This invention relates generally to computed tomograph (CT) imaging and, more particularly, to detectors utilized in connection with CT systems.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

Multislice CT systems are used to obtain data for an increased number of slices during a scan. Known multislice systems typically include detectors generally known as three-dimensional (3-D) detectors. With such 3-D detectors, a plurality of detector cells form separate channels arranged in columns and rows.

A scintillator for a 3-D detector may have scintillator elements with dimensions of about 1×2×3 mm, with narrow gaps of about 100 micrometers, i.e., for example, about 0.004 inches, between adjacent elements. As a result of the small size and the close proximity of the elements, fabrication of such elements is difficult. Further, and in use, a signal impinged upon one scintillator element may be improperly reflected upward or to adjacent elements creating crosstalk and loss of resolution. Also, with such small scintillator elements, the magnitude of the generated optical signal may be small, and any losses that occur can significantly deteriorate signal quality.

It would be desirable to provide a scintillator element that increases the magnitude of the optical signal provided to the photodiode by minimizing the amount of light lost by the element. It would also be desirable to provide a scintillator element having increased spatial resolution. It would further be desirable to provide a scintillator element which includes a light absorber to minimize the amount of light transferred between adjacent elements.

SUMMARY OF THE INVENTION

These and other objects may be attained by a scintillator including a plurality of scintillator elements laid out as an array having gaps between the adjacent elements. The gaps are filled with a composition containing a reflective material, a light absorber, and a castable polymer. In one embodiment, the gaps are filled with a composition of a white, highly diffuse reflective material including titanium dioxide and a castable epoxy. The composition minimizes the amount light that is reflected out of the elements and increases the strength of a signal transmitted to a photodiode located adjacent the scintillator element.

In one embodiment, the scintillator is fabricated by temporally bonding together a stack of scintillator wafers and then cutting the wafers into first bar stacks. After separating the first bar stacks into individual bars, the bars are placed in a fixture with gaps between the bars. The gaps are then filled with the reflective material to form a 2 dimensional array. After the reflective material has cured, a plurality of arrays are stacked and cut into a plurality of second bar stacks. The second bar stacks are then separated into individual second bars and placed in a fixture with gaps between the second bars. The gaps are filled with the reflective material composition to form a 3-D scintillator array having, in one embodiment, 256 scintillator elements.

The above described scintillator provide a higher magnitude signal to the photodiode by minimizing the amount of light that is lost from the scintillator elements. Additionally, the described scintillator includes a light absorber to minimize the amount of light transferred between adjacent scintillator elements.

DETAILED DESCRIPTION

Figure 1:
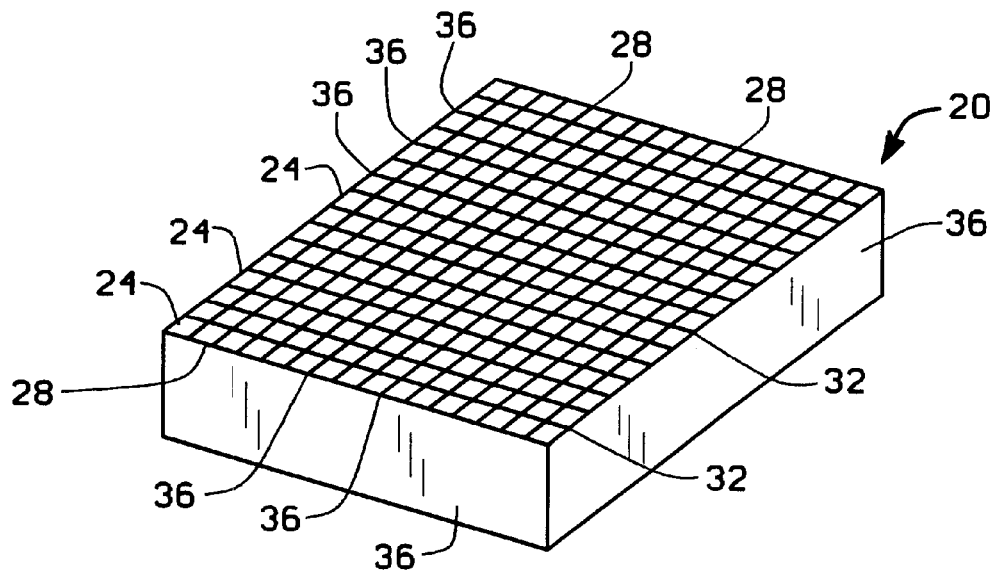
FIG. 1 is a perspective view of a scintillator having a plurality of scintillator elements.

FIG. 1 is a perspective view of a scintillator 20 including a plurality of scintillator elements 24 which are laid out in an array having first gaps 28 and second gaps 32. Scintillator elements 24 are fabricated from, for example, polycrystalline ceramic scintillator material or single crystal scintillation material. To increase the spatial resolution and the strength of a signal supplied to a photodiode located adjacent one of scintillator elements 24, gaps 28 and 32 are filled with a reflective material 36. The width of gaps 28 and 32 may range from about 10 to 160 micrometers, i.e., about 0.5 to 6 mils. Reflective material 36 is cast on the adjacent surfaces of elements 24 so that less of the light signal generated by elements 24 is improperly reflected. In one embodiment, reflective material 36 is selected from silver, aluminum, or gold to provide a reflector having a high reflection and a low absorption of light. In an alternative embodiment, reflective material 36 is a white highly diffuse reflective material including, for example, a composition of titanium dioxide ($TiO_2$) and a castable polymer. The composition of reflective material 36 includes about 20% to 70% by weight TiO$_2$ and a castable epoxy. In another embodiment, a light absorber, for example, chromium oxide (Cr$_2$O$_3$) can be added to the composition to reduce crosstalk between scintillator elements 24.

Figure 2:
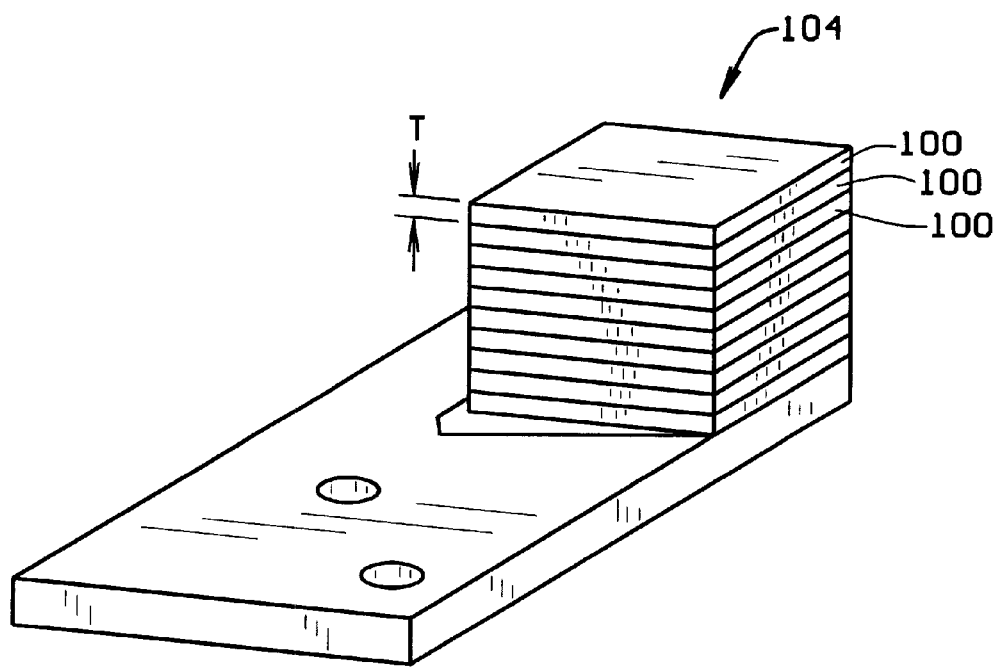
FIG. 2 is a perspective view of a stack of scintillator wafers.
Figure 3:
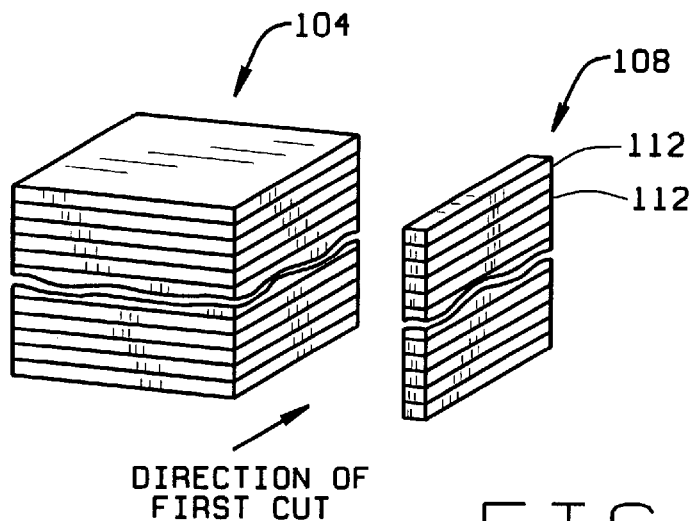
FIG. 3 is a perspective view of a stack of bars cut from the wafer shown in FIG. 2.

In fabricating photosensitive scintillator 20, and referring to FIGS. 2 and 3, thin scintillator wafers 100 are ground or lapped to a preselected thickness T, for example, 3 mm. Wafers 100 are then temporally bonded together using a low melting point adhesive or other temporary adhesive to form a stack 104. Stack 104 is cut into first bar stacks 108 using an inner diameter (ID) saw or wire saw (not shown). In one embodiment, first bar stacks 108 are cut using an inner diameter saw (not shown). The saw has a blade having an inner circumference cutting edge and is used to accurately cut first bar stacks 108 approximately 1 mm wide. After cutting first bar stacks 108, the temporary adhesive bond is broken and first bar stacks 108 are separated into individual bars 112.

Figure 4:
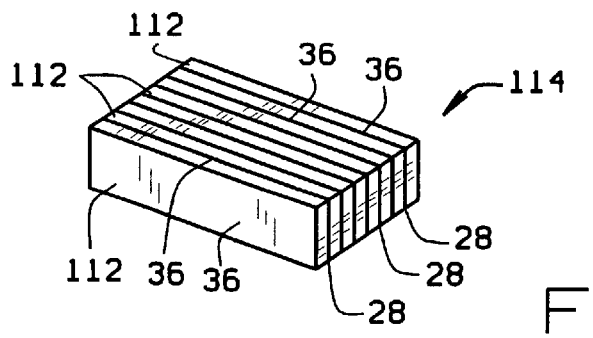
FIG. 4 is a perspective view of the bar stack shown in FIG. 3 after separating the stack into bars with the gaps filled with a reflective material.
Figure 5:
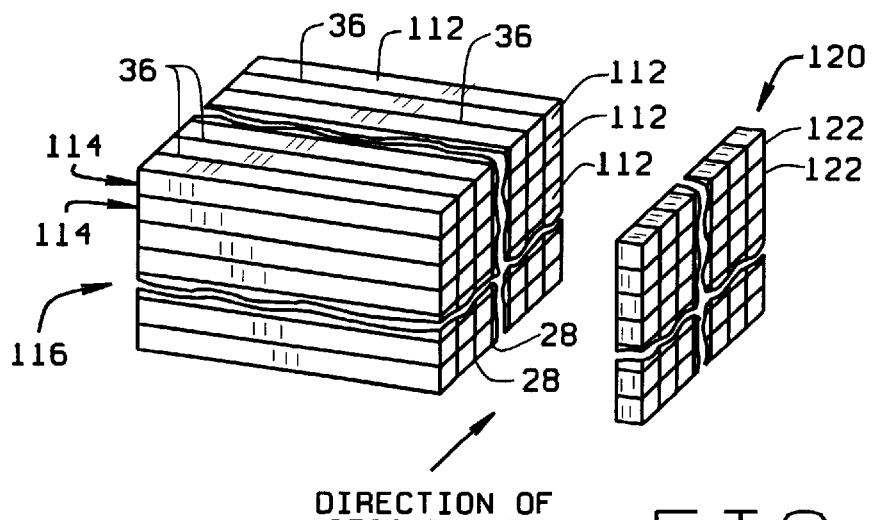
FIG. 5 is a perspective view of a second bar stack cut from the stack shown in FIG. 4.
Figure 6:
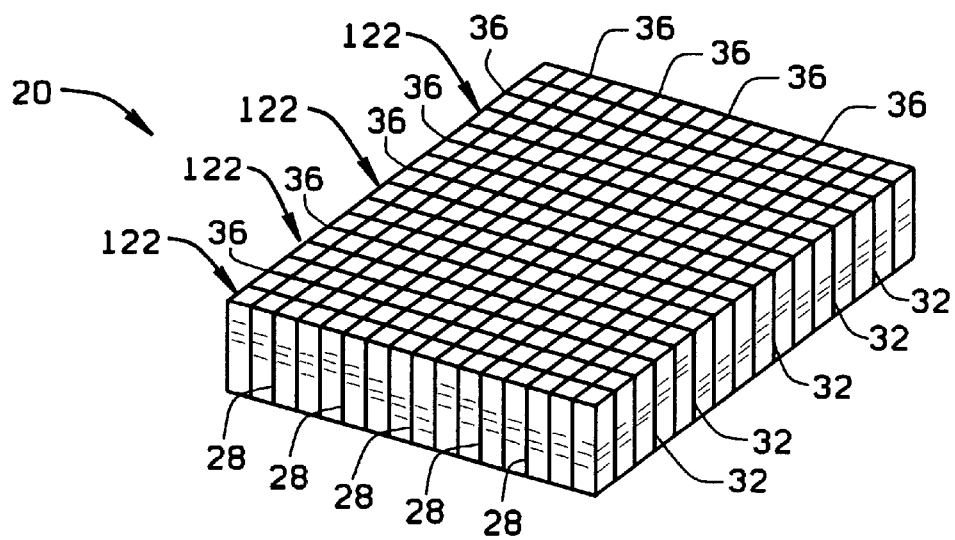
FIG. 6 is a perspective view of the scintillator after second casting.

Referring to FIG. 4 and 5, individual bars 112 are placed into a fixture (not shown) and bonded in an array 114 so that bars 112 are spaced apart from each other forming gaps 28. In one embodiment, sixteen bars are placed in the fixture having gaps 28 of about 4 mils in width. After filling gaps 28 with reflective material 36 and allowing material 36 to cure on adjacent surfaces of bars 112, array 114 is removed from the fixture. A plurality of bonded arrays 114 are then stacked together to form a second stack 116, for example, of ten arrays 114. Second stack 116 is then cut in a manner similar to first bar stacks 108 but perpendicular to the length of bars 112 to create second bar stacks 120. In one embodiment, second bar stacks 120 are 2 mm wide. After separating second bar stacks 120 into individual second bars 122, second bars 122 are placed in a fixture (not shown) so that second bars 122 are spaced apart from each other forming gaps 32. In one embodiment as shown in FIG. 6, sixteen second bars are placed in the fixture with gaps 32 equal in width to gaps 28. After bonding in an array, gaps 32 are filled with cast reflective material 36 in a manner similar to gaps 28. After material 36 has cured and reflective material 36 is cast to the outer periphery, finished scintillator 20 having elements 24 is removed from the fixture.

In one embodiment, wafers 100 are 50 mm square and at least 3 mm thick with finished elements 24 having dimensions of 3 mm high, 2 mm long and 1 mm wide. Of course, various embodiments are possible, including wafers 100 being 1 mm thick so that bars 112 are 3 mm wide and the second cut creates 2 mm long second bars 122. The resulting elements 24 would be the same size as described above.

Figure 7:
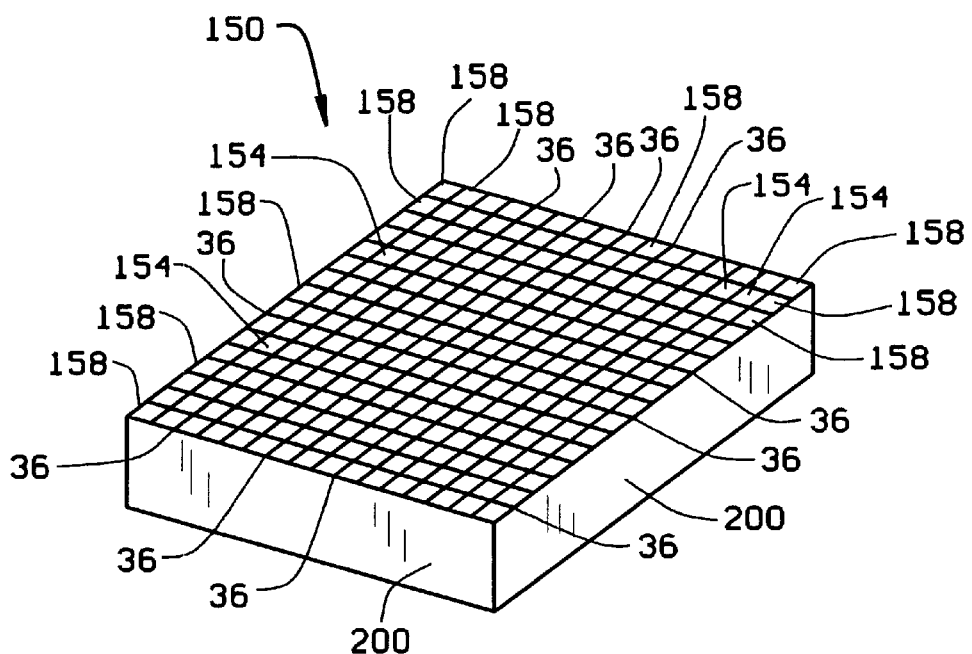
FIG. 7 is a perspective view of an alternative embodiment of scintillator shown in FIG. 1 with the outer reflector having a different composition.

In an alternative embodiment shown in FIG. 7, scintillator 150 includes scintillator elements having eight adjacent elements are identified as interior elements 154 and all other scintillator elements are identified as edge elements 158. Scintillator 150 is fabricated identically to scintillator 20 except a second reflective material 200 is cast adjacent outer periphery of edge elements 158. The composition of second reflective material 200 includes less light absorber, for example, chromium oxide, than reflective material 36. Reflective material 200 allows edge elements 158 to create a higher strength signal than elements 154 as a result of the reduced light absorber content. The higher strength signal increases uniformity by compensating for the light lost at the edges of scintillator 150.

The above described apparatus and method produces a scintillator that increases the signal to the photodiode at the outer periphery by increasing the amount of light that is reflected to the photodiode. Additionally, the described scintillator includes a light absorber to minimize the amount of light transferred between adjacent scintillator elements. In addition, the described scintillator compensates for gain variations of the outer elements and improves the light output uniformity of the scintillator.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A scintillator for a computed tomograph machine, said scintillator comprising:

a plurality of scintillator elements arranged in an array; and a diffuse reflective material filling gaps between adjacent scintillator elements and cured on adjacent surfaces of said elements, said reflective material comprising a composition of TiO$_2$, Cr$_2$O$_3$, and a castable polymer.

2. A scintillator in accordance with claim 1 wherein said TiO$_2$ comprises between about 20% and 70% by weight of said composition.

3. A scintillator in accordance with claim 1 wherein said castable polymer is epoxy.

4. A scintillator in accordance with claim 1 wherein said reflective material has a thickness in a range of between about 10 and 160 micrometers.

5. A scintillator in accordance with claim 1 wherein all of said scintillator elements of said scintillator are separate scintillator elements having said filled gaps therebetween.

6. A scintillator for a computed tomography system, said scintillator comprising:

a plurality of scintillator elements arranged in an array; and a first reflective material positioned adjacent an outer periphery of edge elements of said array, said first reflective material comprising TiO$_2$, Cr$_2$O$_3$, and a castable polymer;

wherein all of said scintillator elements of said scintillator are separate elements joined by a castable, second reflective material positioned between adjacent said elements, said second reflective material comprising TiO$_2$, Cr$_2$O$_3$, and a castable polymer.

7. A scintillator in accordance with claim 6 wherein an amount of Cr$_2$O$_3$ in said first reflective material is less than an amount of Cr$_2$O$_3$ in said second reflective material.

\* \* \* \* \*